US006300097B1

(12) United States Patent
Black et al.

(10) Patent No.: US 6,300,097 B1
(45) Date of Patent: Oct. 9, 2001

(54) **SIGNAL PEPTIDASE POLYPEPTIDES OF *STAPHYLOCOCCUS AUREUS***

(75) Inventors: Michael T. Black, Chester Springs; Karen M. O'Dwyer, Phoenixville, both of PA (US)

(73) Assignee: SmithKline Beecham PLC (GB)

( * ) Notice: Subject to any disclaimer, the term of this patent is extended or adjusted under 35 U.S.C. 154(b) by 0 days.

(21) Appl. No.: 09/344,686

(22) Filed: Jun. 25, 1999

Related U.S. Application Data

(62) Division of application No. 08/940,767, filed on Sep. 30, 1997, now Pat. No. 5,977,085.
(60) Provisional application No. 60/027,220, filed on Oct. 1, 1996, provisional application No. 60/027,218, filed on Sep. 30, 1996, and provisional application No. 60/027,075, filed on Sep. 30, 1996.

(51) Int. Cl.$^7$ ............................. C12P 21/06; C12P 21/04; C12N 9/00; C07H 21/00; A61K 48/00

(52) U.S. Cl. ..................... 435/69.1; 435/70.1; 435/183; 435/252.3; 435/254.1; 435/320.1; 435/325; 435/455; 435/471; 514/44; 536/23.1; 536/23.2; 536/23.7

(58) Field of Search .................................. 435/69.1, 70.1, 435/183, 252.3, 254.11, 320.1, 325, 455, 471; 514/44; 536/23.1, 23.2, 23.7

(56) References Cited

U.S. PATENT DOCUMENTS 5,977,085 * 11/1999 Black et al. ........................... 514/44

OTHER PUBLICATIONS

Bowie et al ; Science ; vol. 247; 1306–1310, 1990.*
Houghten et al; Vaccines 86; Edited by Brown, Chanock and Lerner; Cold Spring Harbor Laboratory, 1986.*
Allsop, et al; "Penem Inhibitors of a Bacterial Signal Peptidase" *Bioorganic & Medicinal Chemistry Letters*, vol. 5, No. 5, pp. 443–448 (1995).
Michael T. Black, "Evidence that the Catalytic Activity of Prokaryote Leader Peptidase Depends upon the Operation of a Serine–Lysine Catalytic Dyad" *Journal of Bacteriology*, vol. 175, No. 16, pp. 4957–4961, Aug., 1993.
Black, et al, "Inhibitors of Bacterial Signal Peptidases" *Current Pharmaceutical Design*, vol.4 pp. 133–154, (1998).
Black, et al, "On the Catalytic Mechanism of Prokaryotic Leader Peptidase 1" *Biochem J*. vol. 282, pp. 539–543, (1992).
Cregg, et al, "Molecular Cloning and Expression of the spsB Gene Encoding an Essential Type I Signal Peptidase from *Staphlococcus Aureus*" *Journal of Bacteriology*, vol. 178, No. 19, pp. 5712–5718, Oct., 1996.
Dalbey, et al, "The Chemistry and Enzymology of the Type I Signal Peptidases" *Protein Science*, vol. 6, pp. 1129–1138, (1996).

Dalbey, et al, "Leader Peptidase Catalyzes the Release of Exported Proteins from the Outer Surface of the *Escherichia Coli* Plasma Membrane" *The Journal of Biological Chemistry*, vol. 260, No. 29, pp. 15925–15931, Dec. 15, 1985.
Takayasu Date, "Demonstration by a Novel Genetic Technique That Leader Peptidase Is an Essential Enzyme of *Escherichia Coli*" *Journal of Bacteriology*, vol. 154, No. 1, pp. 76–83, Apr., 1983.
Fleischmann, et al, "Whole–Genome Random Sequencing and Assembly of *Haemophilus Influenzae* Rd" *Science*, vol. 269, Jul. 28, 1995.
Fraser, et al, "The Minimal Gene Complement of *Mycoplasma Genitalium*" *Science*, vol. 270, Oct. 20, 1995.
Hoang, et al, "*Bacillus amyloliquefaciens* Posseses a Second Type I Signal Peptidase with Extensive Sequence Similarity to Other *Bacillus SPases*" *Biochimica et Biophysica Acta*, vol. 1269, pp. 64–68, (1995).
Inada, et al, "Conditionally Lethal Amber Mutations in the Leader Peptidase Gene of *Escherichia coli*" *Journal of Bacteriology*, vol. 171, No. 1, pp. 585–587, Jan. 1989.
Lih–Ling Lin, et al, "Isolation and Characterization of Noncleavable (Ind–) Mutants of the LexA Repressor of *Escherichia coli* K–12" *Journal of Bacteriology*, vol. 170, No. 5, May, 1988.
Meijer, et al, "The endogenous *Bacillus subtilis* (natto) plasmids pTA 1015 and pTA1040 contain signal peptidase–encoding genes: identification of a of a new structural module on cryptic plasmids" *Molecular Microbiology*, vol. 17, No. 4, pp. 621–631.
Packer, et al, "Cloning and Sequence Analysis of a Signal Peptidase I from the Thermophilic Cyanobacterium Phormidium Laminosum" *Plant Molecular Biology*, vol. 27, pp. 199–204, (1995).
Simonen, et al, "Protein Secretion in Bacillus Species" *Microbiological Reviews*, pp. 109–137 Mar. 1993.
Slilaty, et al, "Lysine–156 and serine–119 are required for LexA repressor cleavage: A possibe mechanism" *Proc. Natl. Acad. Sci.* USA, vol. 84, pp. 3987–3991, Jun., 1987.

(List continued on next page.)

*Primary Examiner*—Lynette R. F. Smith
*Assistant Examiner*—Padma Baskar
(74) *Attorney, Agent, or Firm*—Edward R. Gimmi; Thomas S. Deibert; William T. King

(57) ABSTRACT spsB polypeptides and DNA (RNA) encoding such spsB and a procedure for producing such polypeptides by recombinant techniques is disclosed. Also disclosed are methods for utilizing such spsB for the treatment of infection, particularly bacterial infections. Antagonists against such spsB and their use as a therapeutic to treat infections, particularly bacterial infections are also disclosed. Also disclosed are diagnostic assays for detecting diseases related to the presence of spsB nucleic acid sequences and the polypeptides in a host. Also disclosed are diagnostic assays for detecting polynucleotides encoding spsB and for detecting the polypeptide in a host.

6 Claims, 3 Drawing Sheets

OTHER PUBLICATIONS

Sung, et al, "Identification of Potential Active–site Residues in the *Escherichia coli* Leader Peptidase" *The Journal of Biological Chemistry*, vol. 267, No. 19, pp. 13154–13159, Jul. 5, 1992.

Tschantz, et al, "A Serine and a Lysine Residue Implicated in the Catalytic Mechanism of the *Escherichia coli* Leader Peptidase" *The Journal of Biological Chemistry*, vol. 268, No. 36, pp. 27349–27354, Dec. 25, 1993.

van Dijl, et al, "Molecular cloning of the *Salmonella typhimurium* lep gene in *Escherichia coli*" *Mol. Gen. Genet.*, vol. 223, pp. 233–240 (1990).

van Dijl, et al, "Non–functional expression of *Escherichia coli* signal peptidase I in *Bacillus subtilis*" *Journal of General Microbiology*, vol. 137, pp. 2073–2083, (1991).

van Dijl, et al, "Signal peptidaseI of *Bacillus subtilis*: patterns of conserved amino acids in prokaryotic and eukaryotic type I signal peptidase" *EMBO*, vol. 11, pp. 2819–2828, (1992).

van Dijl, et al, "Identification of the Potential Active Site of the Signal Peptidase SipS of *Bacillus subtilis*" *The Journal of Biological Chemistry*, vol. 270, No. 8, pp. 3611–3618, Feb. 24, 1995.

Wickner, et al, "The Enzymology of Protein Translocation Across the *Escherichia coli* Plasma Membrane" *Annu. Rev. Biochem.*, vol. 60, pp. 101–124, (1991).

Wolfe, et al, "Sequence of the Leader Peptidase Gene of *Escherichia coli* and the Orientation of Leader Peptidase in the Bacterial Envelope" *The Journal of Biological Chemical*, vol. 258, No. 19, pp. 12073–12080, Oct. 10, 1983.

Zhang, et al, "Analysis of a *Streptococcus pneumoniae* gene encoding signal peptidase I and overproduction of the enzyme" *Gene*, vol. 194, pp. 249–255 (1997).

Sambrook, et al, "Molecular Cloning, A Laboratory Manual" Second Edition *Cold Spring Harbor Laboratory Press*, 1989.

Meijer, et al, SwissProt Submission, Accession No. P41026, Feb. 1, 1995.

Meijer, et al, SwissProt Submission, Accession No. P41027, Feb. 1, 1995.

Akagawa, et al, SwissProt Submission, Accession No. P42959, Nov. 1, 1995.

Hoang, et al, SwissProt Submission, Accession No. P42668, Nov. 1, 1995.

* cited by examiner

FIGURE 1.   spsB cloned DNA sequence [SEQ ID NO:1]

```
  1   ttgaaaaaag aattattgga atggattatt tcaattgcag tcgcttttgt 51   cattttattt atagtaggta aatttattgt tacaccatat acaattaaag 101   gtgaatcaat ggatccaact ttgaaagatg gcgagcgagt agctgtaaac 151   attattggat ataaaacagg tggtttggaa aaaggtaatg tagttgtctt 201   ccatgcaaac aaaaatgatg actatgttaa acgtgtcatc ggtgttcctg 251   gtgataaagt agaatataaa aatgatacat tatatgtcaa tggtaaaaaa 301   caagatgaac catatttaaa ctataattta aaacataaac aaggtgatta 351   cattactggg actttccaag ttaaagattt accgaatgcg aatcctaaat 401   caaatgtcat tccaaaaggt aaatatttag ttcttggaga taatcgtgaa 451   gtaagtaaag atagccgtgc gtttggcctc attgatgaag accaaattgt 501   tggtaaagtt tcatttagat tctggccatt tagtgaattt aaacataatt 551   tcaatcctga aaatactaaa aattaa
```

FIGURE 2.  spsB predicted amino acid sequence [SEQ ID NO:2]

1   MKKELLEWII  SIAVAFVILF  IVGKFIVTPY  TIKGESMDPT  LKDGERVAVN

51   IIGYKTGGLE  KGNVVVFHAN  KNDDYVKRVI  GVPGDKVEYK  NDTLYVNGKK

101   QDEPYLNYNL  KHKQGDYITG  TFQVKDLPNA  NPKSNVIPKG  KYLVLGDNRE

151   VSKDSRAFGL  IDEDQIVGKV  SFRFWPFSEF  KHNFNPENTK  N

FIGURE 3.  spsA and spsB cloned DNA sequences and predicted coding sequences
[SEQ ID NO:3]

spsA coding (underlined)

tagaacagcattttatgggatcgaaaaaggagtgacatc<u>gtgaaaaaagttgtaaaatatttgatttcat</u>
<u>tgatacttgctattatcattgtactgttcgtacaaacttttgtaatagttggtcatgtcattccgaataa</u>
<u>tgatatgtcgccaacccttaacaaaggggatcgtgttattgtaaataaaattaaagttacatttaatcaa</u>
<u>ttgaataatggtgatatcattacatataggcgtggtaacgagatatatactagtcgaattattgccaaac</u>
<u>ctggtcaatcaatggcgtttcgtcagggacaattataccgtgatgaccgaccggttgacgcatcttatgc</u>
<u>caagaacagaaaaattaaagattttagtttgcgcaatttttaaagaattagatggagatattataccgcct</u>
<u>aacaatttgttgtgctaaatgatcatgataacaatcagcatgattctagacaatttggtttaattgata</u>
<u>aaaggatattattggtaatataagtttgagatattatcctttttcaaaatggacgattcagttcaaatc</u>
<u>ttaa</u>aaagaggtgtcaaaattgaaaaaagaattattggaatggattatttcaattgcagtcgcttttgtc
attttatttatagtagggtaaatttattgttacaccatatacaattaaaggtgaatcaatggatccaactt
tgaaagatggcgagcgagtagctgtaaacattattggatataaaacaggtggtttggaaaaaggtaatgt
agttgtcttccatgcaaacaaaatgatgactatgttaaacgtgtcatcggtgttcctggtgataaagta
gaatataaaaatgatacattatatgtcaatggtaaaaaacaagatgaaccatatttaaactataatttaa
aacataaacaaggtgattacattactgggactttccaagttaaagatttaccgaatgcgaatcctaaatc
aaatgtcattccaaaaggtaaatatttagttcttggagataatcgtgaagtaagtaaagatagccgtgcg
tttggcctcattgatgaagaccaaattgttggtaaagtttcatttagattctggccatttagtgaattta
aacataatttcaatcctgaaaatactaaaaattaatatgaaacaaatacaacatcgtttgtcggttttaa
tactgataaacgatgttttattttgttagt  spsB coding (bold underlined)

SIGNAL PEPTIDASE POLYPEPTIDES OF *STAPHYLOCOCCUS AUREUS*

RELATED PATENT APPLICATION

This application is a division of Ser. No. 08/940,767 filed Sep. 30, 1997, now U.S. Pat. No. 5,977,085 which claims benefit of U.S. patent application Ser. No. 60/027,218, filed Sep. 30, 1996, Ser. No. 60/027,220, filed Oct. 1, 1996, and Ser. No. 60/027,075, filed Sep. 30, 1996.

FIELD OF THE INVENTION

This invention relates, in part, to newly identified polynucleotides and polypeptides; variants and derivatives of these polynucleotides and polypeptides; processes for making these polynucleotides and these polypeptides, and their variants and derivatives and antagonists of the polypeptides; and uses of these polynucleotides, polypeptides, variants, derivatives and antagonists. In particular, in these and in other regards, the invention relates to polynucleotides and polypeptides of spsB, hereinafter referred to as "spsB".

BACKGROUND OF THE INVENTION

The majority of proteins that are translocated across one or more membranes from the site of synthesis are initially synthesized with an N-terminal extension known as a signal, or leader, peptide (Wickner, W., et al, (1991). *Ann. Rev. Biochem.* 60:101–124). Proteolytic cleavage of the signal sequence to yield the mature protein occurs during, or shortly after, the translocation event and is catalyzed in both prokaryotes and eukaryotes by enzymes known as signal, or leader, peptidases (SPases). The bacterial SPases are membrane proteins consisting of a single polypeptide anchored to the membrane by one (Gram-positive ($G^+$) and Gram-negative ($G^-$) bacteria) or two ($G^-$ bacteria) transmembrane sections. Predicted amino acid sequences of bacterial SPases show a high level of similarity and are known for *Escherichia coli* (Wolfe, P. B, et al, (1983) *J. Biol. Chem.* 258:12073–12080), *Pseudomonas fluorescens* (Black, M. T., et al, (1992). *Biochem. J.* 282:539–543), *Salmonella typhimurium* (van Dijl, J. M., et al, (1990). *Mol. Gen. Genet.* 223:233–240), *Haemophilus influenzae* (Fleischmann, R. D., et al, (1995). *Science* 269:496–512), *Phormidium laminosum* (Packer, J. C., et al, (1995). *Plant Mol. Biol.* 27:199–204. K. Cregg, et al: Signal peptidase from *Staphylococcus aureus* Manuscript JB765–96), *Bradyrhizobium japonicum* (Müller, P., et al, (1995). *Mol. Microbiol.* 18:831–840), *Rhodobacter capsulatus* (Klug, G., et al, (1996). GenBank entry, accession number 268305), *Bacillus subtilis* (two chromosomal and two of plasmid origin (Akagawa, et al, (1995) *Microbiol.* 141:3241–3245; Meljer, W. J. J., et al, (1995). *Mol. Microbiol.* 17:621–631; van Dijl, J. M., et al, (1992). *EMBO J.* II:2819–2828), *Bacillus licheniformis* (Hoang, V., et al, (1993). Sequence P42668 submitted to emb1/genbank/ddbj data banks.), *Bacillus caldotyricus* (van Dijl, J. M. (1993). Sequence p41027, submitted to embl1/genbank/ddbj data banks), *Bacillus amyloliquifaciens* (two chromosomal genes) (Hoang, V. and J. Hofemeister. (1995). *Biochim. Biophys. Acta* 1269:64–68; van Dijl, J. M. (1993). Sequence p41026, submitted to emb1/genbank/ddbj data banks) and a partial sequence has been reported for *Bacillus pumilis* (Hoang, V. and J. Hofemeister. (1995). *Biochim. Biophys. Acta* 1269:64–68). These enzymes have been collectively defined as type-1 signal pepidases (van Dijl, J. M., et al, (1992). *EMBO J.* II11:2819–2828). Although the amino acid sequences of fifteen bacterial SPases (and a sixteenth partial sequence) have now been reported, the best studied examples are leader peptidase (LPase or LepB) from *E. coli* and a SPase from *B. subtilis* (SipS).

It has been demonstrated that LPase activity is essential for cell growth in *E. coli*. Experiments whereby expression of the lepB gene, encoding LPase, was regulated either by a controllable ara promoter (Dalbey, R. E. and Wickner. 260:15925–15931) or by partial deletion of the natural promoter (Date, T. (1983). *J. Bacteriol.* 154:76–83) indicated that minimization of LPase production was associated with cessation of cell growth and division. In addition, an *E. coli* strain possessing a mutated lepB gene (*E. coli* IT41) has been shown to have a drastically reduced growth rate and display a rapid and pronounced accumulation of preproteins when the temperature of the growth medium is elevated to 42° C. (Inada, T., et al, (1988). *J. Bactericol.* 171:585–587). These results infer that there is no other gene product in *E. coli* that can substitute for LPase and that lepB is a single-copy gene in the *E. coli* chromosome. This is in contrast to at least two species within the $G^+$ Bacillus genus, *B. subtilis* and *B. amyloliquifaciens*. It is known that there are at least two homologous SPase genes in each of these Bacillus species. The sipS gene can be deleted from the chromosome of *B. subtilis* 168 without affecting cell growth rate or viability under laboratory conditions to yield a mutant strain that can still process preα-amylase (K. M. Cregg and M. T. Black, unpublished). A putative SPase sequence (Akagawa, et al, (1995) *Microbiol.* 141:3241–3245) may be the gene-product responsible for this activity and/or *B. subtilis* may harbor more than two SPase genes. Two or more genes encoding distinct SPase homologues reside on the chromosome of the closely related species *B. amyloliquifaciens* (Hoang, V. and J. Hofemeister. (1995). *Biochim. Biophys. Acta* 1269:64–68) and there is evidence to suggest that *B. Japonicum* may possess more than one SPase (Müller, P., et al, (1995). *Mol. Microbiol.* 18:831–840; Müiller, P., et al, (1995). *Planta* 197:163–175). Although SPase sequences from seven genera of G+ bacteria are now known, only the single Bacillus genus amongst the G+ eubacteria has been investigated with respect to SPase characteristics. It was therefore considered of interest to determine whether a G+ eubacterium that, unlike *B. subtilis* and *B. amyloliquifaciens*, is not known for exceptional secretion activity has genes encoding more than one SPase with overlapping substrate specificities or whether it resembles *E. coli* and *H. influenzae* (and possibly other G– eubacteria)more closely in that it has a single SPase gene. The recent publication of the entire genomic sequence of the obligate G+-like intracellular bacterium *Mycoplasma genitalium* also reveals an interesting feature relating to heterogeneity amongst SPases (Fraser, C. M., et al, (1995). *Science* 270:397–403). Inhibitors of *E. coli* LPase have bean reported (Allsop, A. E., et al, 1995. *Bioorg, & Med. Chem. Letts.* 5:443–448).

Evidence has accumulated to suggest that LPase belongs to a new class of serine protease that does not utilize a histamine as a catalytic base (Black, M. T., et al, (1992). *Biochem. J.* 282:539–543; Sung, M. and R. E. Dalbey. (1992). *J. Biol. Chem* 267:13154–13159) but may instead employ a lysine side-chain to fulfill this role (Black, M. T. (1993). *J. Bacteriol.* 175:4957–4961; Tschantz, W. R., et al, (1993). *J. Biol. Chem.* 268:27349–27354). These observations and comparisons with Lex A from *E. coli* led to the proposal that a serine-lysine catalytic dyad, similar to that thought to operate during peptide bond hydrolysis catalyzed by LexA (Slilaty, S. N. and J. Little. (1987). *Proc. Natl. Acad. Sci. USA* 84:3987–3991), may operate in LPase (Black, M. T. (1993). *J. Bacteriol.* 175:4957–4961). Similar observations have since been made for SPase from *B. subtilis* (van Dijl, J. M., et al, (1995). *J. Biol. Chem.* 270:3611–3618) and for the Tsp periplasmic protease from *E. coli* (Keiler, K. C. and R. T. Sauer. (1995). *Biol. Chem.* 270:28864–28868); the similarities of SipS to LexA have been suggested to extend to several regions of primary structure (van Dijl, J. M., et al, (1995). *J. Biol. Chem.* 270:3611–3618). The serine and lysine residues (90 and 145 respectively in *E. coli* LPase numbering) known to be critical for catalytic activity in both *E. coli* LPase (Black, M. T. (1993). *J. Bacteriol.* 175:4957–4961; Tschantz, W. R., et al, (1993) *J. Biol. Chem.* 268:27349–27354) and *B. subtilis* SPase (van Dijl, J. M., et al, (1995). *J. Biol. Chem.* 270:3611–3618) and thought to form a catalytic dyad are both conserved in the *S. aureus* protein SpsB (S36 and K77). In addition, the aspartate at position 155 (280 in *E. coli* LPase numbering) is also conserved (this residue appears important for activity of the SipS SPase (van Dijl, J. M., et al, (1995). *J. Biol. Chem.* 270:3611–3618) but less so for LPase from *E. coli* (Sung, M. and R. E. Dalbey. (1992). *J. Biol. Chem* 267:13154–13159).). The present invention provides, among other things, this novel SPase (spsB) from *S. aureus*.

Clearly, there is a need for factors that may be used to screen compounds for antibiotic activity and which may also be used to determine their roles in pathogenesis of infection, dysfunction and disease. There is a need, therefore, for identification and characterization of such factors which can play a role in preventing, ameliorating or correcting infections, dysfunctions or diseases.

The polypeptide of the present invention has amino acid sequence homology to known serine proteases.

SUMMARY OF THE INVENTION

Toward these ends, and others, it is an object of the present invention to provide polypeptides, inter alia, that have been identified as novel spsB by homology between the amino acid sequence set out in FIG. 2 and known amino acid sequences of other proteins such as *Bacillus subtillis* sipS.

It is a further object of the invention, moreover, to provide polynucleotides that encode spsB, particularly polynucleotides that encode the polypeptide herein designated spsB.

In a particularly preferred embodiment of this aspect of the invention the polynucleotide comprises the region encoding spsB in the sequence set out in FIG. 1 [SEQ ID NO:1], or a fragment, analogue or derivative thereof.

In another particularly preferred embodiment of the present invention there is a novel serine protease protein from *Staphylococcus aureus* comprising the amino acid sequence of FIG. 2 [SEQ ID NO:2], or a fragment, analogue or derivative thereof.

In accordance with this aspect of the present invention there is provided an isolated nucleic acid molecule encoding a mature polypeptide expressible by the *Staphylococcus aureus* bacterial clone contained in NCIMB Deposit No. 40771.

In accordance with this aspect of the invention there are provided isolated nucleic acid molecules encoding spsB, particularly *Staphylococcus* spsB, including mRNAs, cDNAs, genomic DNAs and, in further embodiments of this aspect of the invention include biologically, diagnostically, prophylactically, clinically or therapeutically useful variants, analogs or derivatives thereof, or fragments thereof, including fragments of the variants, analogs and derivatives, and compostions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of spsB and polypeptides encoded thereby.

In accordance with this aspect of the invention there are provided novel polypeptides of Staphylococcus referred to herein as spsB as well as biologically, diagnostically, prophylactically, clinically or therapeutically useful fragments, variants and derivatives thereof, variants and derivatives of the fragments, and analogs of the foregoing, and compostions comprising same.

Among the particularly preferred embodiments of this aspect of the invention are variants of spsB polypeptide encoded by naturally occurring alleles of the spsB gene.

In a preferred embodiment of this aspect of the invention there are provided methods for producing the aforementioned spsB polypeptides.

In accordance with yet another aspect of the present invention, there are provided inhibitors to such polypeptides, useful as antibacterial agents, including, for example, antibodies.

In accordance with certain preferred embodiments of this aspect of the invention, there are provided products, compositions and methods, inter alia: assessing spsB expression; to treat upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis); assaying genetic variation; and administering a spsB polypeptide or polynucleotide to an organism to raise an immunological response against a bacteria, especially a Staphylococcus.

In accordance with certain preferred embodiments of this and other aspects of the invention there are provided polynucleotides that hybridize to spsB polynucleotide sequences.

In certain additional preferred embodiments of this aspect of the invention there are provided antibodies against spsB polypeptides.

In accordance with yet another aspect of the present invention, there are provided spsB antagonists which are also preferably bacteriostatic or bacteriocidal.

In a further aspect of the invention there are provided compositions comprising a spsB polynucleotide or a spsB polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Staphylococcus aureus* spsB [SEQ ID NO:1].

FIG. 2 shows the amino acid sequence of *Staphylococcus aureus* spsB [SEQ ID NO:2] deduced from the polynucleotide sequence of FIG. 1.

FIG. 3 shows the polynucleotide and deduced amino acid sequences of *Staphylococcus aureus* spsA and spsB [SEQ ID NO:3].

GLOSSARY

The following illustrative explanations are provided to facilitate understanding of certain terms used frequently herein, particularly in the Examples. The explanations are provided as a convenience and are not limitative of the invention.

spsB-BINDING MOLECULE, as used herein, refers to molecules or ions which bind or interact specifically with spsB polypeptides or polynucleotides of the present invention, including, for example enzyme substrates, cell membrane components and classical receptors. Binding between polypeptides of the invention and such molecules, including binding or binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polyncleotide sequence.

IDENTITY or SIMILARITY, as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology,* von Heinje, G., Academic Press, 1987; *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Methods commonly employed to determine identity or similarity between sequences include, but are not limited to those disclosed in Carillo, H., and Lipman, D., SIAM *J. Applied Math.,* 48:1073 (1988). Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAS with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other posttranslational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS— STRUCTURE AND MOLECULAR PROPERTIES,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODI-FICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N. Y. Acad. Sci. 663: 48–62 (1992). It will be appreciated, as is well known and as noted above, that polypeptides are not always entirely linear. For instance, polypeptides may be generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli.* Accordingly, when glycosylation is desired, a polypeptide should be expressed in a glycosylating host, generally a eukaryotic cell. Insect cell often carry out the same posttranslational glycosylations as mammnalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleoticle. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

DETAILED DESCRIPTION OF THE INVENTION

The present invention relates to novel spsB polypeptides and polynucleotides, among other things, as described in greater detail below. In particular, the invention relates to polypeptides and polynucleotides of a novel spsB gene of *Staphylococcus aureus*, which is related by amino acid sequence homology to *Bacillus subtillis* sipS polypeptide. The invention relates especially to spsB having the nucleotide and amino acid sequences set out in FIG. 1 and FIG. 2 respectively, and to the spsB nucleotide and amino acid sequences of the DNA in NCIMB Deposit No. 40771, which is herein referred to as "the deposited clone" or as the "DNA of the deposited clone." It will be appreciated that the nucleotide and amino acid sequences set out in FIGS. 1 [SEQ ID NO:1] and 2 [SEQ ID NO:2] were obtained by sequencing the DNA of the deposited clone. Hence, the sequence of the deposited clone is controlling as to any discrepancies between it (and the sequence it encodes) and the sequences of FIG. 1 [SEQ ID NO:1] and FIG. 2 [SEQ ID NO:2].

Polynucleotides

In accordance with one aspect of the present invention, there are provided isolated polynucleotides which encode the spsB polypeptide having the deduced amino acid sequence of FIG. 2 [SEQ ID NO:2].

Using the information provided herein, such as the polynucleotide sequence set out in FIG. 1 [SEQ ID NO:1], a polynucleotide of the present invention encoding spsB polypeptide may be obtained using standard cloning and screening procedures, such as those for cloning and sequencing chromosomal DNA fragments from *Staphylococcus aureus* WCUH 29 cells as starting material, followed by obtaining a full length clone. For example, to obtain a polynucleotide of the invention sequence, such as that sequence given in FIG. 1 [SEQ ID NO:1] typically a library of clones of chromosomal DNA of *Staphylococcus aureus* WCUH 29 in *E.coli* or some other suitable host is probed with a radiolabelled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in FIG. 1 [SEQ ID NO:1] was discovered in a DNA library derived from *Staphylococcus aureus* WCUH 29.

SpsB of the invention is structurally related to other spsB proteins, as shown by the results of sequencing the DNA encoding spsB of the deposited clone. The DNA sequence thus obtained is set out in FIG. 1 [SEQ ID NO:1]. It contains an open reading frame encoding a protein of having about the number of amino acid residues set forth in FIG. 2 [SEQ ID NO:2] with a deduced molecular weight that can be calculated using amino acid residue molecular weight values well known in the art. The protein exhibits greatest homology to *Bacillus subtillis* sipS protein among known proteins. spsB of FIG. 2 [SEQ ID NO:2] has homoogy with the amino acid sequence of *Bacillus subtillis* sipS.

Polynucleotides of the present invention may be in the form of RNA, such as MRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 [SEQ ID NO:1]. It also may be a polynucleotide with a different sequence, which, as a result of the redundancy (degeneracy) of the genetic code, encodes the polypeptide of FIG. 2 [SEQ ID NO:2].

Polynucleotides of the present invention which encode the polypeptide of FIG. 2 [SEQ ID NO:2] may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad Sci., USA* 86: 821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37: 767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly bacterial, and more particularly the *Staphylococcus aureus* spsB having the amino acid sequence set out in FIG. 2 [SEQ ID NO:2]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of spsB set out in FIG. 2 [SEQ ID NO:2]; variants, analogs, derivatives and fragments thereof, and fragments of the variants, analogs and derivatives.

Further particularly preferred in this regard are polynucleotides encoding spsB variants, analogs, derivatives and fragments, and variants, analogs and derivatives of the fragments, which have the amino acid sequence of spsB polypeptide of FIG. 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of spsB. Also especially preferred in this regard are conservative substitutions. Most highly preferred are polynucleotides encoding polypeptides having the amino acid sequence of FIG. 2 [SEQ ID NO:2], without substitutions.

Further preferred embodiments of the invention are polynucleotides that are at least 70% identical over their entire length to a polynucleotide encoding spsB polypeptide having the amino acid sequence set out in FIG. 2 [SEQ ID NO:2], and polynucleotides which are complementary to such polynucleotides. Alternatively, most highly preferred are polynucleotides that comprise a region that is at least 80% identical over their entire length to a polynucleotide encoding spsB polypeptide of the *Staphylococcus aureus* DNA of the deposited clone and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more prefered.

Preferred embodiments in this respect, moreover, are polynucleotides which encode polypeptides which retain substantially the same biological function or activity as the mature polypeptide encoded by the DNA of FIG. 1 [SEQ ID NO:1].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding spsB and to isolate cDNA and genomic clones of other genes that have a high sequence similarity to the spsB gene. Such probes generally will comprise at least 15 bases. Preferably, such probes will have at least 30 bases and may have at least 50 bases. Particularly preferred probes will have at least 30 bases and will have 50 bases or less.

For example, the coding region of the spsB gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, including SEQ ID NOS:3 and 4, derived from the sequences of SEQ ID NOS:1 and 2 may be used in the processes herein as described, but preferably for PCR, to determine whether or not the *Staphylococcus aureus* genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A deposit containing a *Staphylococcus aureus* spsB bacterial clone has been deposited with the National Collections of Industrial and Marine Bacteria Ltd. (NCIMB), 23 St. Machar Drive, Aberdeen AB2 1RY, Scotland on Sep. 11, 1995 and assigned NCIMB Deposit No. 40771. The *Staphylococcus aureus* bacterial clone deposit is referred to herein as "the deposited clone" or as "the DNA of the deposited clone."

The deposited material is a bacterial clone that contains the full length spsB DNA, referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a spsB polypeptide which has a deduced amino acid sequence of 151 amino acids in length, as set forth in FIG. 2 [SEQ ID NO:2], and has a deduced molecular weight of 21.692 kilodaltons.

The invention also relates to fragments, analogs and derivatives of these polypeptides. The terms "fragment," "derivative" and "analog" when referring to the polypeptide of FIG. 2 [SEQ ID NO:2], means a polypeptide which retains essentially the same biological function or activity as such polypeptide. Thus, an analog includes a proprotein which can be activated by cleavage of the proprotein portion to produce an active mature polypeptide.

The fragment, derivative or analog of the polypeptide of FIG. 2 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of spsB set out in FIG. 2 [SEQ ID NO:2], variants, analogs, derivatives and fragments thereof, and variants, analogs and derivatives of the fragments. Alternatively, particularly preferred embodiments of the invention in this regard are polypeptides having the amino acid sequence of the spsB, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the spsB polypeptide of FIG. 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the spsB. Also especially preferred in this regard are conservative substitutions. Most highly preferred are polypeptides having the amino acid sequence of FIG. 2 [SEQ ID NO:2] without substitutions.

The polypeptides and polynucleotides of the present invention are preferably provided in an isolated form, and preferably are purified to homogeneity.

The polypeptides of the present invention include the polypeptide of FIG. 2 [SEQ ID NO:2] (in particular the mature polypeptide) as well as polypeptides which have at least 70% identity to the polypeptide of FIG. 2 [SEQ ID NO:2], preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of spsB, most particularly fragments of spsB having the amino acid set out in FIG. 2 [SEQ ID NO:2], and fragments of variants and derivatives of the spsB of FIG. 2 [SEQ ID NO:2].

In this regard a fragment is a polypeptide having an amino acid sequence that entirely is the same as part but not all of the amino acid sequence of the aforementioned spsB polypeptides and variants or derivatives thereof.

Such fragments may be "ftee-standing," ie., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a spsB polypeptide of the present comprised within a precursor polypeptide designed for expression in a host and having heterologous pre and pro-polypeptide regions fused to the amino terminus of the spsB fragment and an additional region fused to the carboxyl terminus of the fragment. Therefore, fragments in one aspect of the meaning intended herein, refers to the portion or portions of a fusion polypeptide or fusion protein derived from spsB.

Representative examples of polypeptide fragments of the invention, include, for example, fragments from amino acid number 1–20, 21–40, 41–60, 61–80, 81–100, and 101–151, and any combination of these 20 amino acid fragments.

In this context "about" herein includes the particularly recited ranges larger or smaller by several, a few, 5, 4, 3, 2 or 1 amino acid at either extreme or at both extremes.

Preferred fragments of the invention include, for example, truncation polypeptides of spsB. Truncation polypeptides include spsB polypeptides having the amino acid sequence of FIG. 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous seres of residues, one including the amino terminus and one including the carboxyl terminus. Frggments having the size ranges set out about also are preferred embodiments of truncation fragments, which are especially preferred among fragments generally. Degradation forms of the polypeptides of the invention in a host cell, particularly a Staphylococcus, are also preferred.

Also preferred in this aspect of the invention are fragments characterized by structural or functional attributes of spsB. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of spsB, and combinations of such fragments.

Preferred regions are those that mediate activities of spsB. Most highly preferred in this regard are fragments that have a chemical, biological or other activity of spsB, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY,* (1986) and Sambrook et al., *MOLECULAR CLONING: A LABORATORY MANUAL,* 2nd Ed., Cold Spring Harbor Laboratory Press, Cold Spring Harbor, N.Y. (1989).

Polynucelotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *MOLECULAR CLONING: A LABORATORY MANUAL,* 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct MRNA transcription. Representatives of such promoters include, but are limited to, the phage lambda PL promoter, the E. coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

Representative examples of appropriate hosts include bacterial cells, such as streptococci, staphylococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and PSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the E. coli lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al, *Journal of Molecular Recognition,* Vol. 8 52–58 (1995) and K. Johanson et al., *The Journal of Biological Chemistry,* Vol. 270, No. 16, pp 9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

spsB polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide assays

This invention is also related to the use of the spsB polynucleotides to detect complementary polynucleotides such as, for example, as a diagnostic reagent. Detection of spsB in a eukaryote, particularly a mammal, and especially a human, will provide a diagnostic method for diagnosis of a disease. Eukaryotes (herein also "individual(s)"), particularly mammals, and especially humans, infected with an organism comprising the spsB gene may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., *Nature,* 324: 163–166 (1986) prior to analysis. RNA or cDNA may also be used in the same ways. As an example, PCR primers complementary to the nucleic acid encoding spsB can be used to identify and analyze spsB presence and/or expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled spsB RNA or alternatively, radiolabeled spsB antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with doulble-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g. Myers et al., *Science,* 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA,* 85:4397–4401 (1985)).

Thus, the detection of a specific DNA sequence may be achieved by methods such as hybridization, RNase protection, chemical cleavage, direct DNA sequencing or the use of restriction enzymes, e.g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding spsB can be used to identify and analyze mutations. These primers may be used for amplifying spsB DNA isolated from a sample derived from an individual.

The invention provides a process for diagnosing, disease, preferably bacterial infections, more preferably *Staphylococcus aureus,* and most preferably upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis)., comprising determining from a sample derived from an individual a increased level of expression of polynucleotide having the sequence of FIG. 1 [SEQ ID NO:1]. Increased expression of spsB polynucleotide can be measured using any on of the methods well known in the art for the quantation of polynucleotides, such as, for example, PCR, RT-PCR, RNase protection, Northern blotting and other hybridization methods.

Polypeptide assays

The present invention also relates to a diagnostic assays such as quantitative and diagnostic assays for detecting levels of spsB protein in cells and tissues, including determination of normal and abnormal levels. Thus, for instance, a diagnostic assay in accordance with the invention for detecting over-expression of spsB protein compared to normal control tissue samples may be used to detect the presence of an infection, for example. Assay techniques that can be used to determine levels of a spsB protein, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to spsB, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, suchas those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilised to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against spsB may be employed to inhibit and/or treat infections, particularly bacterial infections and especially upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis)

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanised"; where the complimentarily determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunisation will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264,16985), coprecipitation of DNA with calcium phosphate (Benvenisty & Reshef, PNAS,1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

spsB-binding molecules and assays

This invention also provides a method for identification of molecules, such as binding molecules, that bind spsB. Genes encoding proteins that bind spsB, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (199 1). Also, a labeled ligand can be photoaffinity linked to a cell extract. Polypeptides of the invention also can be used to assess spsB binding capacity of spsB-binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be strucural or functional mimetics.

Antagonists and—assays and molecules

The invention also provides a method of screening compounds to identify those which block (antagonist) the action of spsB polypeptides or polynucleotides, such as its interaction with spsB-binding molecules.

For example, to screen for antagoists, a synthetic reaction mix, a cellular compartment, such as a membrane, cell envelope or cell wall, or a preparation of any thereof, may be prepared from a cell that expresses a molecule that binds spsB. The preparation is incubated with labeled spsB in the absence or the presence of a candidate molecule which may be a spsB antagonist. The ability of the candidate molecule to bind the binding molecule is reflected in decreased binding of the labeled ligand. Molecules which bind gratuitously, i.e., without inducing the effects of spsB on binding the spsB binding molecule, are most likely to be good antagonists.

spsB-like effects of potential antagonists may by measured, for instance, by determining activity of a reporter system following interaction of the candidate molecule with a cell or appropriate cell preparation, and comparing the effect with that of spsB or molecules that elicit the same effects as spsB. Reporter systems that may be useful in this regard include but are not limited to colorimetric labeled substrate converted into product, a reporter gene that is responsive to changes in spsB activity, and binding assays known in the art.

Another example of an assay for spsB antagonists is a competitive assay that combines spsB and a potential antagonist with membrane-bound spsB-binding molecules, recombinant spsB binding molecules, natural substrates or ligands, or substrate or ligand mimetics, under appropriate conditions for a competitive inhibition assay. spsB can be labeled, such as by radioactivity or a colorimetric compound, such that the number of spsB molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing spsB-induced activities, thereby preventing the action of spsB by excluding spsB from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules).

Preferred potential antagonists include compounds related to and derivatives of spsB.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block serine protease protein mediated mammalian cell invasion by, for example, initiating phosphorylation of mammalian tyrosine kinases (Rosenshine et al., *Infect. Immun.* 60:2211 (1992); iii) to block bacterial adhesion between mammalian extracellular matrix proteins and bacterial serine protease proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists may be employed for instance to inhibit upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Vaccines

Another aspect of the invention relates to a method for inducing an immunological response in an individual, particularly a mammal which comprises inoculating the individual with spsB, or a fragment or variant thereof, adequate to produce antibody to protect said individual from infection, particularly bacterial infection and most particularly Staphylococcus infections. Yet another aspect of the invention relates to a method of inducing immunological response in an individual which comprises, through gene therapy, delivering gene encoding spsB, or a fragment or a variant thereof, for expressing spsB, or a fragment or a variant thereof in vivo in order to induce an immunological response to produce antibody to protect said individual from disease.

A further aspect of the invention relates to an immunological composition which, when introduced into a host capable or having iduced within it an immunological response, induces an immunological response in such host to a spsB or protein coded therefrom, wherein the composition comprises a recombinant spsB or protein coded therefrom comprising DNA which codes for and expresses an antigen of said spsB or protein coded therefrom.

The spsB or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of *Staphylococcus aureus* infection in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain spsB, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeplides discussed above or the antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Staphylococcus wound infections.

Many orthopaedic surgeons consider that humans with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 $\mu$g/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 $\mu$g/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing the serine protease protein.

All references and patent applications disclosed herein are incorporated by reference herein in their entirety.

In order to facilitate understanding of the following example certain frequently occurring methods and/or terms will be described.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

The following bacterial strains were used in these Examples: E. coli XL-1-Blue, JM109 and 1T41, S. aureus RN4220, H (ATCC13801), Oxford (ATCC9144) and WCUH29 (NCIMB 40771). S. aureus strains were known in tryptone soya broth (TSB, Oxoid) or in Luria-Bertani broth (Sambrook, J., et al, (1989). Molecular Cloning: a Labaoratory manual. $2^{nd}$ Cold Spring Harbor Laboratory Press Cold Spring Harbor N.Y.). E. coli was cultured in Luria-Bertani broth. For solid medium. 1.5% (w/v) agar was added. Where appropriate, the medium was supplemented with 100 $\mu$g ml ampicillin for E. coli and 5 $\mu$g ml chloramphenicol for S. aureus. The S. aureus WCUH29 genomic library was constructed by Stratagene in the vector $\lambda$ZapII. The $\lambda$ZapII s. aureus H library was constructed in this laboratory according to the instructions of the manufacturers of $\lambda$ZapII (Stratagene). All shuttle vector constructs that were transferred from E. coli to S. aureus WCUH29 were first used to transform the restriction-minus S. aureus strain RN4220 and plasmid purified there from was used to transform S. aureus WCUH29. Plasmids used in this study are described in the examples below.

Example 1

DNA Cloning (A) DNA techniques and materials

Plasmid DNA was isolated using the RPM Kit (Bio 101 Inc.) or the Wizard Midiprep DNA Purification System (Promega). PCR products were isolated by horizontal agarose gel Li electrophoresis, treated with Agarase (Boehringer Mannheim) and purified with the Wizard DNA Clean-Up System (Promega). Chromosomal DNA was isolated from E. coli and S. aureus using either the Genomic DNA Purification Kit (Bacterial) (Advanced Genetic Technologies Corp.) or following published procedures (Marmur, J. (1961). J. Mol. Biol. 3:208–218). An incubation and the appropriate quantity of lysotaphin (Applied Microbiology Inc.) was included during the preparation of plasmid and chromosomal DNA from S. aureus to facilitate cell lysis. $\lambda$ZapII library clones were excised and recircularized to form recombinant phagemid as described in the manufacturer's instructions. Procedures for DNA restriction and dephophorylation, agarose gel electrophoresis, PCR and transformation of competent E. coli cells were performed essentially as described in Sambrook et al. (Sambrook, J., et al, (1989). Molecular Cloning: a Laboratory manual. $2^{nd}$ Cold Spring Harbor Laboratory Press Cold Spring Harbor N.Y.). Electrocompetent S. aureus cells were prepared as described by Schenk and Laddaga (Schenk, S. and R. A. Laddaga. 1992. Micorobiol. Letts. 94:133–138) with the following modifications: the bacteria were grown in TSB and washed at 2500×g for 5 times at 20° C. Competent cells and plasmid DNA were electroporated in 1 mm gap electroporation cuvettes at 20° C., 100Ω, 25 μF, and 2.3 kV in a Gene Pulser apparatus with pulse controller (Bio-Rad Laboratories Ltd.). Restriction enzymes and calf intestine alkaline phosphatase were purchased from Promega, ligations were performed using a DNA Ligation Kit (Amersham) as described in the manufacturer's instructions, sequencing was performed using the Sequence Version 2.0 DNA Sequencing Kit (Amersham). PCR reactions, optimized using the Opti-Prime Kit (Stratagene), were performed on the Hybaid OmniGene thermal cycler using either Pfu DNA polymerase (Promega) and the products cloned using the Ta-Cloning Kit (Invitrogen), the pGEM-T Cloning Kit (Promega) or the DNA Ligation Kit (Amersham). Oligonucleotides were synthesized by Cruachem Ltd or R&D Systems Europe Ltd. PCR primer sequences [SEQ ID NO:4–13], with intentional differences from template sequence shown in upper case, were as follows:

Primer A (g/a)tNgg(a/t)(c/t)tNcc(a/t)gg(a/t)ga(a/t)aN(a/t)(g/a)t [SEQ ID NO:4]
(Primer A RtNggWYtNccWggWgaWaNWRt [SEQ ID NO:4])
Primer B c(t/g)(a/g)tt(a/g)tc(t/a)cccatNa(t/c)(a/g)aa(a/g)ta [SEQ ID NO:5]
(Primer B cKRttRtcWcccatNaYRaaRta [SEQ ID NO:5])
Primer C tgGAaTTCAtgaaaaaagaaCtGttggaatggattatttc [SEQ ID NO:6]
Primer D atttgtAAGCtTttaGttttGgtGttttcaggattgaaa [SEQ ID NO:7]
Primer E ctgGATCCcgcttgattagttttattga [SEQ ID NO:8]
Primer F ttGGtACCttttgacacctcttttaag [SEQ ID NO:9]
Primer G aaGGtACCtatgaaacaaatacaacatc [SEQ ID NO:10]
Primer H atGAAtTCtcaatataattgtgacactc [SEQ ID NO:11]
Primer I atattagagcgataattcc [SEQ ID NO:12]
Primer J gttcatttgctattcttc [SEQ ID NO:13]

(B) PCR Cycle Conditions for Primer Pairs

A+B [SEQ ID NO:4 and 5]: 5 min at 94° C., 30 cycles of [1 min at 94° C., 1 min at 42° C., 1 min at 72° C.], 5 mins at 72° C.

C+D [SEQ ID NO:6 and 7]: 5 mins at 94° C., 15 cycles of [1 min at 94° C., 1 min at 50° C., 1 min at 72° C.], 5 mins at 72° C.

E+F [SEQ ID NO:8 and 9]: 5 mins at 94° C., 15 cycles of [1 min at 94° C., 1 min at 60° C., 2 mins at 72° C.], 5 mins at 72° C.

G+H [SEQ ID NO:10 and 11]: 5 mins at 94° C., 15 cycles of [1 min at 94° C., 1 min at 45° C., 2 mins at 72° C., 2 mins at 72° C.], 5 mins at 72° C.

I+J [SEQ ID NO:12 and 13]: 5 mins at 94° C., 30 cycles of [1 min at 94° C., 1 min at 42° C., 2 mins at 72° C.], 5 mins at 72° C.

DNA was Southern blotted from 0.7% (w/v) agarose gels onto nylon membranes (Hybond-N', Amersham) as described in the manufacturer's instructions. For library screening purposes plaques were transferred to nylon membranes (Hybond-N, Amersham) as described in the manufacturer's instructions. Membranes were hybridized with either oligonucleotide or whole gene probes labeled using the ECL 3'-oligolabelling kit or the ECL random prime labeling kit (Amersham) as appropriate. Washing and detection steps were performed as described in the manufacturer's instructions. All sequence data manipulation was performed with the Wisconsin Package (7).

(C) PCR Cloning

A strategy was devised to clone SPase by PCR using primers A+B [SEQ ID NO:4 and 5] (see Materials and Methods). A fragment of DNA of the expected length, based upon the known size of SPases from Bacillus, was obtained from a preparation of genomic DNA from S. aureus Oxford. The 163 bp of sequence so derived is highly homologous to 163 bp of the sipS gene from B. subtillis implying that a fragment of a gene encoding a type-I SPase had been cloned. The PCR product was labeled and used to probe a λZap-II library of S. aureus WCUH29 genomic DNA in order to obtain full sequence information. A positive clone was identified and the recombinant plasmid (pKC10) excised, cut with several restriction enzymes, blotted and probed with the same labeled DNA fragment as aforementioned. A Sall-digested pKC10 preparation was religated to form plasmid pKC11. The DNA sequence of 3093 bp of insert DNA was determined by oligonucleotide walking in both directions from within the sequence originally derived by PCR. FIG. 3 shows 1220 nucleotides of DNA sequence from the chromosome of S. aureus WCUH29 of which nucleotides 817–1025 represent the probe region. The probe sequence comprises part of a potential open reading frame (ORF) which in its entirely encodes a polypeptide of 151 amino acid residues with a calculated molecular mass of 21,692 Da and with a single section of hydrophobic residues close to the N-terminus that probably form a single transmembrane anchor. The small surface-exposed domain and single transmembrane anchor are typical of SPases from G+ eubacteria. The predicted protein has high homology with all known G+SPases and the gene has been named spsB (signal peptidase from Staphylococcus). It is noteworthy that the highest levels of sequence similarity are in regions of the protein corresponding to the most highly conserved regions of known SPases. All three of these regions within the B. subtilis SPase, and two within LPase from E. coli contain at least one residue that is critical for catalytic activity (Black, M. T. (1993). J. Bacteriol. 175:4957–4961; Tschantz, W. R., et al, (1993) J. Biol. Chem. 268:27349–27354; van Dijl, J. M., et al, (1995). J. Biol. Chem. 270:3611–3618). A second ORF, named spsA, proximal to the spsB gene (separated by 15 nucleotides) putatively encodes a protein of 174 amino acid residues with a calculated molecular mass of 20,146 Da. Sequence comparison reveals that this protein in also similar to known SPase sequences. An optimized alignment of SpsB with SpsA results in 62% similarly and 31% identify between the two sequences. The regions of highest sequence conservation are concentrated within or close together. However, a surprising observation is the fact that neither the serine nor the lysine residue known to be essential for catalytic activity in type-I SPases are conserved in SpsA. In order to ascertain that the existence of spsA is not peculiar to the WCUH29 strain of S. aureus a λZapII library of DNA isolated from S. aureus strain H was probed with the probe originally used to identify clones containing the spsA/B genes from strain WCUH29. Close homologues of both spsA and spsB were also discovered in S. aureus H; SpsA also lack active-site serine and lysine residues.

Example 2

Expression of the spsB Gene in E. coli

Significant expression levels of active LPase from lepB cloned on a plasmid can be obtained in E. coli (Dalbey, R. E. and Wickner. 260:15925–15931; Wolfe, P. B, et al, (1983) J. Biol. Chem. 258:12073–12080). Although the gene was transcribed and translated, LPase did not assemble correctly in the membrane and had no detectable activity in vitro using cell-free extracts of B. subtilis producing E. coli LPase as an enzyme source (van Dijl, J. M., et al, (1991). J. Gen. Microbiol. 137:2073–2083). Conversely, functional expression of the B. subtilis sipS-encoded SPase in E. coli has been demonstrated and was instrumental in the successful cloning of the sipS gene (van Dijl, J. M., et al, (1992). EMBO J.

11:2819–2828). It is clear from the work described that SipS assembled in the correct orientation in the *E. coli* membrane. However, the activity monitored was solely cleavage of an artificial engineered preprotein, one property of which was an extension of the central hydrophobic region of the signal sequence. It was therefore of interest to determine whether the spsB gene could be functionally expressed in *E. coli* and whether the SPase so produced could catalyze the cleavage of signal sequences from natural *E. coli* preproteins. The spsB gene was amplified from Plasmid PKC11 by PCR using primer pair C+D containing mismatches to the template sequence. Each PCR primer was designed to effect two major changes: introduction of a restriction site at each end of the gene to facilitate cloning (EcoRI at the 5' end and HindIII at the 3' end) and changes to 3 bases that produced silent codon changes; the latter changes were effected in order to minimize restrictions on mRNA translation due to staphylococcal codons that are comparatively rare in *E. coii* and to change the TTG initiation codon to an ATG codon. The PCR product was cloned into plasmid pDB575 to form pKC16. The correct sequence of the cloned insert was confirmed pKC16 was used to transform *E. coli* XL1-Blue to ampicillin resistance and cells examined for production of SpsB after induction with isopropyl-β-thiogalactopyranoside (IPTG). Cultures were grown to mid-log phase, induced and harvested 2.5 hours post-induction. Cell lysates were analyzed by SDS-PAGE. It is clear that significant quantities of SpsB were produced by *E. coli* (pKC16) even in the absence of induction of SpsB expression with IPTG. An increase in strain density (lanes 3 and 5) compared with the control (lanes 2 and 4) at a position corresponding to a protein of –Mr21,000 is apparent both with (lanes 4 and 5) and without (lanes 2 and 3) IPTG induction.

Experiments were carried out to determine whether SpsB is functionally active in *E. coli*. The *E. coli* strain IT41 has a single mutant copy of the lepβ gene and is Ts for preprotein processing (Inada, T., et al, (1988). *J. Bacteriol.* 171:585–587). The strain has been used extensively in investigations of LPase function and activity as the rate of preprotein processing and rate of cell division are severely compromised at 42° C. but can be restored by complementation with plasmid-borne active LPase (Black, M. T. (1993). *J. Bacteriol.* 175:4957–4961; Black, M. T., et al, (1992). *Biochem. J.* 282:539–543; Inada, T., et al, (1988). *J. Bacteriol.* 171:585–587). It should be noted that no unambiguous correlation between *E. coli* IT41 growth rate and the rate of pre-protein processing is demonstrably apparent under these experimental conditions (Black, M. T. (1993). *J. Bacteriol.* 175:4957–4961; Black, M. T., et at, (1992). *Biochem. J.* 282:539–543; Sung, M. and R. E. Dalbey. (1992). *J. Biol. Chem* 267:13154–13159; Tschantz, W. R., et al, (1993) *J. Biol. Chem.* 268:27349–27354). *E. coli* IT41 was transformed with pKC16 and with the control plasmid pDB575. Growth of *E. coli* IT41 (pDB575) and *E. coli* IT41 (pKC16) at 42° C. was monitored as optical density at 540 mm over a period of 8 hours in the absence of IPTg (due to a possible toxic effect of high level SpsB production). There is a very substantial increase in the growth rate of *E. coli* IT41 (pKC16) as compared with *E. coli* IT41 (pDB575) indicating functional expression of SpsB. The generation time of 1½ hours is similar to that observed when *E. coli* IT41 was transformed with a plasmid which over-expresses authentic *E. coli* LPase and was grown under the same conditions (Black, M. T. (1993). *J. Bacteriol.* 175:4957–4961). However, as *E. coli* IT41 has been known to revert to wild-type growth characteristics it was considered necessary to ascertain that the sequence of the mutant lepB gene had not changed during the course of the experiment. As the sequence of the *E. coli* IT41 lepB gene has not previously been determined it was necessary to also determine this sequence from the stocks of cells that were used for the complementation studies. The *E. coli* IT41 (*E. coli* IT41 grown at the permissive temperature of 28° C. and *E. coli* IT41 (pKC16) after growth at 42° C.) and cloned into the plasmid PBluescriptII SK. The sequence of each PCR product was then determined and found to be identical. IN each case only a single base change was apparent as compared with the wild-type *E. coli* lepB sequence. The base change in the *E. coli* IT41 lepB gene in each case was a C→T transition at nucleotide position 115 in the lepB coding sequence, a mutation that changes a glutamine codon (Gln-39 in LPase) to a TAG amber termination codon. As it has been demonstrated that the sequence of the *E. coli* IT41 lepB gene had not changed during the course of the experiment. It can therefore be concluded that SpsB complements the growth of the *E. coli* preprotein processing Ts mutant IT41 in vivo. This infers that SpsB assembles correctly in the *E. coli* plasma membrane and that it catalyses the processing of all essential *E. coli* preproteins.

Example 3

Expression Analyses

SDS-PAGE was carried out essentially according to Laemmli (Laemmli, U.K. (1970). *Nature* (London) 227:680–685) using the Mini PROTEAN II apparatus (Bio-Rad Laboratories, Inc.). Cultures were grown to mid-log phase and then induced by addition of 1 mM IPTG. CiGls were harvested 2.5 hours post-induction total cell lysates prepared as outlined in Sambrook et al. (Kurosky, A., et al, *Proc. Natl. Acad. Sci. USA* 77:3388–3392), and proteins separated by electrophoresis through a 15% (w/v) acrylamide resolving gel.

For complementation studies *E. coli* IT41 was transformed with appropriate plasmids and ampicillin-resistant tranformants picked from agar plates grown at 28° C. were incubated in broth overnight at the permissive temperature of 28° C. Cultures were diluted 100-fold into flesh medium and incubated with shaking at the non-permissive temperature of 42° C. OD at 540 nm was recorded at 30 min intervals for a period of 8 hours.

Selection for double crossover plasmid integration/resolution events and plasmid curing was carried out using *S. aureus* WCUH29(pIMO5) and WCUH29(pIMII) grown overnight at 28° C. in the presence of chloramphenicol. The cultures were diluted 100-fold into fresh medium without chloramphenicol and incubated at 43° C. Cultures were grown at 43° C. in the absence of chloramphenicol for 56 hours to reduce the plasmid copy number during which time the cultures were subinoculated 5 times (twice daily) into fresh medium. Samples were then diluted and plated at 28° C. in the presence (integration/resolution) or absence (plasmid curing) of chloramphenicol.

Identification of colonies with a plasmid-borne copy of spsB derived from the chromosome was performed as follows. Colonies were seeded into 100 μl TSB containing 5 μg/ml chloramphenicol in the wells of microliter plates and incubated overnight at 28° C. (Rlfai, S., et al, (1989) *J. Clin Microbiol.* 27:504–506). The microtitre plates were centrifuged at 1000×g for 10–20 mins and the supernatant discarded. Pellets were resuspended in 20 μl 50 mM Tris-HCl, pH 7.5, 145 mM NaCl containing 3 units lysotaphin and incubated for 30–45 mins at 37° C. Cell lysates (2 μl) were spotted onto nylon membranes (Hybond-N+, Amersham) and the DNA denatured and fixed to the membrane as described in the manufacturer's instructions. Membranes were hybridized with either the spsB gene or the downstream flanking region labeled using the ECL random prime labeling kit (Amersham) as described in the manufacturer's instructions.

Example 4
Essentiality of the spsB Gene in S. aureus.

As it is known that B. subtilis and B. amyloliquifaciens each possess at least two SPase genes it was of interest to determine whether S. aureus also has a second gene encoding in active SPase. Attempts were therefore made to delete the spsB gene from the chromosome of S. aureus WCUH29 by double-crossover homologous recombination using the plasmid pTS 1 which contains a chloramphenicol-resistance determinant active in S. aureus, a TsG replication function derived from a mutant of PE194 (Villafane, R., et al, (1987). J. Bacteriol. 169:4822–4829), and pUC18 enabling replication and selection in E. coli (a gift from Dr. t. Foster, Trinity College, Dublin). The general strategy and detail of the method are as that described for E. coli by Hamilton et al. (Hamilton, C. M., et al, 1989. New method for generating deletions and gene replacements in Escherichia coli. J. Bacteriol. 171:4617–4622). The essence of the method is that upstream (I) and downstream (D) regions of DNA flanking the gene of interest are cloned into a plasmid with a Ts replication function. Growth at the non-permissive temperature selects for integration by homologous recombination (Campbell-type integration) and subsequent growth of co-integrants at the permissive temperature leads to a second recombination event resulting in plasmid resolution. If the first even takes place at region U and the second event takes place at region D, or vice versa, then the gene of interest will be transferred to the plasmid from the chromosome. If the gene of interest is dispensable then the recombinant plasmid can subsequently be cured from the cell by raising the temperature whereas if the gene is essential the plasmid cannot be cured (or cannot be cured if further recombination events reverse the overall process leading to replacement of the gene to the chromosome). Regions of DNA both upstream and downstream of spsB gene, 850 bp each, were amplified by PCR from plasmid pKC11 using primer pairs E+F and G+H respectively. These pairs generate terminal restriction enzyme sites to facilitate subsequent cloning steps. The PCR products were cloned and ligated via a KpnI site in pUC18 (pIM04) and the DNA sequence ascertained to ensure that no errors had been incorporated during amplification. The 1700 bp fragment was subcloned into the multiple cloning site of pTS1 using BamHI/EcoRI sites and the construct, pIM05 transformed from E. coli into S. aureus RN4220 and then to S. aureus WCUH29 by electroporation. After appropriate temperature cycling to select for integration by homologous recombination into the chromosome and plasmid resolution therefrom, cell lysates from individual colonies were prepared and screened for the presence of plasmids bearing a copy of spsB derived from the chromosome by hybridization to a probe for spsB. One such clone was isolated (pIM11) and its identity confirmed by restriction analysis and Southern blotting. This clone was subjected to temperature cycling at 43° C. in attempt to cure the plasmid from the cell. Cells were plated in the absence of chloramphenicol and 146 colonies replica plated to plates with or without chloramphenicol. 76 colonies grew well in the presence of chloramphenicol, while the remainder showed no or very poor growth. NO plasmid could be isolated from the chloramphenicol-sensitive colonies and in all cases plasmid isolated from the chloramphenicol-resistant colonies possessed wild-type spsB. Two explanations are possible which would account for the appearance of chloramphenicol-sensitive colonies derived from S. aureus (PIM11). One is that spsB is not an essential gene and the other is that pIM11 recombinated with the chromosome, the plasmid was resolved depositing spsB on the chromosome and was subsequently lost from the cell. To distinguish between these two possibilities, genomic DNA was isolated from 10 such colonies, from S. aureus (pIM11) and from S. aureus WCUH29 and oligonucleotide PCR primers I+J used to amplify chromosomal DNA therefrom. The primers correspond to regions of chromosomal DNA that lay upstream and downstream of sequences cloned into pIM11 thereby precluding any possibility of amplification of undetected plasmid-borne target sequences. DNA fragments so derived were size fractionated on an agarose gel and blotted to nylon membranes. Two identical membranes were prepared which were either probed with a labeled oligonucleotide which recognized spsB in order to confirm the presence or absence of spsB or with a labeled oligonucleotide which bound to the downstream flanking region. There were no cases where plasmid pIM11 was lost from S. aureus without first effecting the transfer of spsB back to the chromosome as the amplified fragments were the same size (2,554 bp) as that amplified from S. aureus WCUH29 DNA and the products hybridized to the probes for both spsB and the downstream flanking region. The product obtained by amplifying chromosomal DNA from s. aureus (pIM11) was smaller (1,979 bp) and did not hybridize to the probe for spsB, confirming that spsB had been deleted from the chromosome and that chromosomal and not plasmid DNA had been amplified. These data infer that the type-I SPase encoded by the spsB gene has an indispensable role in preprotein processing in S. aureus and that this activity is essential for the viability of S. aureus. As a control experiment S. aureus WCUH29 was transformed with the plasmid pIM 11 and subjected to temperature-cycling and replica plating as above. Plasmid-borne spsB could readily be removed from spsB merodiploids.

What is claimed is:

1. An isolated polypeptide comprising SEQ ID NO:2.

2. A composition comprising the isolated polypeptide of claim 1 and a carrier.

3. The isolated polypeptide of claim 1, wherein the isolated polypeptide comprises a heterologous amino acid sequence fused to SEQ ID NO:2.

4. A composition comprising the isolated polypeptide of claim 3 and a carrier.

5. The isolated polypeptide of claim 1, wherein the isolated polypeptide consists of SEQ ID NO:2.

6. A composition comprising the isolated polypeptide of claim 5 and a carrier.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 576 base pairs (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:1:

```
TTGAAAAAAG AATTATTGGA ATGGATTATT TCAATTGCAG TCGCTTTTGT CATTTTATTT      60

ATAGTAGGTA AATTTATTGT TACACCATAT ACAATTAAAG GTGAATCAAT GGATCCAACT     120

TTGAAAGATG GCGAGCGAGT AGCTGTAAAC ATTATTGGAT ATAAAACAGG TGGTTTGGAA     180

AAAGGTAATG TAGTTGTCTT CCATGCAAAC AAAAATGATG ACTATGTTAA ACGTGTCATC     240

GGTGTTCCTG GTGATAAAGT AGAATATAAA AATGATACAT TATATGTCAA TGGTAAAAAA     300

CAAGATGAAC CATATTTAAA CTATAATTTA AAACATAAAC AAGGTGATTA CATTACTGGG     360

ACTTTCCAAG TTAAAGATTT ACCGAATGCG AATCCTAAAT CAAATGTCAT TCCAAAAGGT     420

AAATATTTAG TTCTTGGAGA TAATCGTGAA GTAAGTAAAG ATAGCCGTGC GTTTGGCCTC     480

ATTGATGAAG ACCAAATTGT TGGTAAAGTT TCATTTAGAT TCTGGCCATT TAGTGAATTT     540

AAACATAATT TCAATCCTGA AAATACTAAA AATTAA                              576
```

(2) INFORMATION FOR SEQ ID NO:2:

(i) SEQUENCE CHARACTERISTICS:
            (A) LENGTH: 191 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:2:

```
Met Lys Lys Glu Leu Leu Glu Trp Ile Ile Ser Ile Ala Val Ala Phe
 1               5                  10                  15

Val Ile Leu Phe Ile Val Gly Lys Phe Ile Val Thr Pro Tyr Thr Ile
            20                  25                  30

Lys Gly Glu Ser Met Asp Pro Thr Leu Lys Asp Gly Glu Arg Val Ala
        35                  40                  45

Val Asn Ile Ile Gly Tyr Lys Thr Gly Gly Leu Glu Lys Gly Asn Val
    50                  55                  60

Val Val Phe His Ala Asn Lys Asn Asp Asp Tyr Val Lys Arg Val Ile
65                  70                  75                  80

Gly Val Pro Gly Asp Lys Val Glu Tyr Lys Asn Asp Thr Leu Tyr Val
                85                  90                  95

Asn Gly Lys Lys Gln Asp Glu Pro Tyr Leu Asn Tyr Asn Leu Lys His
            100                 105                 110

Lys Gln Gly Asp Tyr Ile Thr Gly Thr Phe Gln Val Lys Asp Leu Pro
        115                 120                 125

Asn Ala Asn Pro Lys Ser Asn Val Ile Pro Lys Gly Lys Tyr Leu Val
    130                 135                 140

Leu Gly Asp Asn Arg Glu Val Ser Lys Asp Ser Arg Ala Phe Gly Leu
145                 150                 155                 160

Ile Asp Glu Asp Gln Ile Val Gly Lys Val Ser Phe Arg Phe Trp Pro
                165                 170                 175

Phe Ser Glu Phe Lys His Asn Phe Asn Pro Glu Asn Thr Lys Asn
            180                 185                 190
```

(2) INFORMATION FOR SEQ ID NO:3:

(i) SEQUENCE CHARACTERISTICS:
        (A) LENGTH: 1220 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

```
TAGAACAGCA TTTTATGGGA TCGAAAAAGG AGTGACATCG TGAAAAAAGT TGTAAAATAT      60
TTGATTTCAT TGATACTTGC TATTATCATT GTACTGTTCG TACAAACTTT TGTAATAGTT     120
GGTCATGTCA TTCCGAATAA TGATATGTCG CCAACCCTTA ACAAAGGGGA TCGTGTTATT     180
GTAAATAAAA TTAAAGTTAC ATTTAATCAA TTGAATAATG GTGATATCAT TACATATAGG     240
CGTGGTAACG AGATATATAC TAGTCGAATT ATTGCCAAAC CTGGTCAATC AATGGCGTTT     300
CGTCAGGGAC AATTATACCG TGATGACCGA CCGGTTGACG CATCTTATGC CAAGAACAGA     360
AAAATTAAAG ATTTTAGTTT GCGCAATTTT AAAGAATTAG ATGGAGATAT TATACCGCCT     420
AACAATTTTG TTGTGCTAAA TGATCATGAT AACAATCAGC ATGATTCTAG ACAATTTGGT     480
TTAATTGATA AAAAGGATAT TATTGGTAAT ATAAGTTTGA GATATTATCC TTTTTCAAAA     540
TGGACGATTC AGTTCAAATC TTAAAAAGAG GTGTCAAAAT TGAAAAAAGA ATTATTGGAA     600
TGGATTATTT CAATTGCAGT CGCTTTTGTC ATTTTATTTA TAGTAGGTAA ATTTATTGTT     660
ACACCATATA CAATTAAAGG TGAATCAATG GATCCAACTT TGAAAGATGG CGAGCGAGTA     720
GCTGTAAACA TTATTGGATA TAAAACAGGT GGTTTGGAAA AAGGTAATGT AGTTGTCTTC     780
CATGCAAACA AAAATGATGA CTATGTTAAA CGTGTCATCG GTGTTCCTGG TGATAAAGTA     840
GAATATAAAA ATGATACATT ATATGTCAAT GGTAAAAAAC AAGATGAACC ATATTTAAAC     900
TATAATTTAA AACATAAACA AGGTGATTAC ATTACTGGGA CTTTCCAAGT TAAAGATTTA     960
CCGAATGCGA ATCCTAAATC AAATGTCATT CCAAAAGGTA AATATTTAGT TCTTGGAGAT    1020
AATCGTGAAG TAAGTAAAGA TAGCCGTGCG TTTGGCCTCA TTGATGAAGA CCAAATTGTT    1080
GGTAAAGTTT CATTTAGATT CTGGCCATTT AGTGAATTTA AACATAATTT CAATCCTGAA    1140
AATACTAAAA ATTAATATGA AACAAATACA ACATCGTTTG TCGGTTTTAA TACTGATAAA    1200
CGATGTTTTA TTTTGTTAGT                                                1220
```

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

```
RTNGGWYTNC CWGGWGAWAN WRT                                              23
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

CKRTTRTCWC CCATNAYRAA RTA                23

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

TGGAATTCAT GAAAAAAGAA CTGTTGGAAT GGATTATTTC                40

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

ATTTGTAAGC TTTTAGTTTT TGGTGTTTTC AGGATTGAAA                40

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

CTGGATCCCG CTTGATTAGT TTTATTGA                28

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

TTGGTACCTT TTGACACCTC TTTTTAAG                28

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

AAGGTACCTA TGAAACAAAT ACAACATC                28

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

ATGAATTCTC AATATAATTG TGACACTC                                28

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

ATATTAGAGC GATAATTCC                                          19

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

GTTCATTTGC TATTCTTC                                           18